United States Patent
Lee et al.

(10) Patent No.: US 10,160,708 B2
(45) Date of Patent: Dec. 25, 2018

(54) SYSTEMS AND METHODS FOR PRODUCING DIMETHYL ETHER FROM NATURAL GAS

(71) Applicant: ExxonMobil Research and Engineering Company, Annandale, NJ (US)

(72) Inventors: Anita S. Lee, Jersey City, NJ (US); Jihad M. Dakka, Whitehouse Station, NJ (US); Arun K. Sharma, Hellertown, PA (US); Michel Daage, Hellertown, PA (US); Preeti Kamakoti, Summit, NJ (US); Ronald Suryo, Lebanon, NJ (US); Chuansheng Bai, Phillipsburg, NJ (US); J. Timothy Cullinane, Montgomery, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/455,181

(22) Filed: Mar. 10, 2017

(65) Prior Publication Data

US 2017/0297986 A1    Oct. 19, 2017

Related U.S. Application Data

(60) Provisional application No. 62/317,703, filed on Apr. 4, 2016.

(51) Int. Cl.
*C07C 41/09* (2006.01)
*C07C 41/01* (2006.01)
(Continued)

(52) U.S. Cl.
CPC ............... *C07C 41/09* (2013.01); *C01B 3/34* (2013.01); *C07C 29/151* (2013.01); *C07C 41/01* (2013.01);
(Continued)

(58) Field of Classification Search
CPC .............. C01B 2203/0233; C01B 3/34; C01B 2203/0238; C01B 2203/062; C07C 41/01; C07C 1/20
See application file for complete search history.

(56) References Cited

U.S. PATENT DOCUMENTS

2015/0018592 A1    1/2015 Schodel et al.

FOREIGN PATENT DOCUMENTS

GB    2097382 A    11/1982

OTHER PUBLICATIONS

Peng et al., Single-Step Syngas-to-Dimethyl Ether Processes for Optimal Productivity, Minimal Emissions, and Natural Gas-Derived Syngas (Ind. Che. Res. 1999, 38, 4381-4388).*

(Continued)

*Primary Examiner* — Jafar F Parsa
(74) *Attorney, Agent, or Firm* — Liza Negron; Chad A. Guice (57) ABSTRACT

Integrated methods and systems are disclosed for the production of dimethyl ether. The method may include reforming natural gas to syngas in a first reactor; contacting the syngas produced in the first reactor with a catalyst system in a second reactor to produce dimethyl ether and carbon dioxide; and supplying steam as a cofeed to at least one of the first reactor and the second reactor in an amount sufficient to achieve a $M_m$ value of 1.4 to 1.8 or to improve the hydrocarbon or oxygenate selectivity.

12 Claims, 4 Drawing Sheets

(51) Int. Cl.
*C01B 3/34* (2006.01)
*C07C 29/151* (2006.01)
(52) U.S. Cl.
CPC ............. *C01B 2203/0216* (2013.01); *C01B 2203/0233* (2013.01); *C01B 2203/06* (2013.01); *C01B 2203/061* (2013.01)

(56) References Cited

OTHER PUBLICATIONS

Stiefel et al., "Direct synthesis of dimethyl ether from carbon-monoxide-rich synthesis gas: Influence of dehydration catalysts and operating conditions", Fuel Processing Technology, Aug. 1, 2011, pp. 1466-1474, vol. 92, No. 8, Elsevier.
International Search Report and Written Opinion PCT/US2017/021704 dated Jun. 12, 2017.

\* cited by examiner

SYSTEMS AND METHODS FOR PRODUCING DIMETHYL ETHER FROM NATURAL GAS

CROSS-REFERENCE TO RELATED APPLICATIONS

This application claims priority to U.S. Provisional Application Ser. No. 62/317,703 filed on Apr. 4, 2016, herein incorporated by reference in its entirety.

FIELD

Embodiments of the invention are generally related to systems and methods for producing dimethyl ether from natural gas.

BACKGROUND

Various processes have been proposed for producing dimethyl ether from natural gas. One such process involves co-feeding natural gas with an enriched oxygen stream to an autothermal reformer to produce syngas. Dimethyl ether may then be produced in a two stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether is a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

SUMMARY

In one aspect, an integrated method is provided for the production of dimethyl ether. The method may include reforming natural gas to syngas in a first reactor; contacting the syngas produced in the first reactor with a catalyst system in a second reactor to produce dimethyl ether and carbon dioxide; and supplying steam as a cofeed to at least one of the first reactor and the second reactor in an amount sufficient to achieve a $M_m$ value of 1.4 to 1.8 wherein $M_m=(H_2-CO_2+H_2O)/(CO+CO_2-H_2O)$ and $H_2$ is moles of $H_2$ fed to the second reactor, $CO_2$ is moles of $CO_2$ fed to the second reactor, CO is moles of CO fed to the second reactor and $H_2O$ is moles of $H_2O$ fed to the second reactor.

In another aspect, a system is provided for the production of dimethyl ether. The system may include a natural gas supply stream; a reverse flow reactor receiving the natural gas supply stream, wherein the reverse flow reactor is adapted to convert the natural gas supply stream to a syngas stream comprising carbon monoxide and hydrogen gas; a dimethyl ether reactor downstream of the reverse flow reactor containing a catalyst system for converting syngas to dimethyl ether; a separator for separating carbon dioxide from the dimethyl ether; a recycle stream for recycling carbon dioxide from the separator to the reverse flow reactor; and a steam supply stream adapted to feed steam to the dimethyl reactor.

DETAILED DESCRIPTION OF THE EMBODIMENTS

Improved systems and methods for producing dimethyl ether from natural gas are disclosed herein. Integrated systems and methods of the present invention generally include a natural gas reformer, such as a reverse flow reactor, which converts a natural gas feed to a syngas product and an integrated dimethyl ether reactor which receives the syngas from the natural gas reformer and produces dimethyl ether as a product. The methods and systems may further include the integration of steam as a cofeed and the use of a catalyst for the in-situ conversion methanol to dimethyl ether in the same reactor as the catalyst for converting syngas to methanol to achieve improved carbon efficiency with low selectivity for hydrocarbons and oxygenates. Advantageous configurations may permit the separation and use of recycle streams having desirable compositions for improving carbon efficiency and thermal efficiency. For example, a CO2-rich stream may be obtained by separation of the product stream of the dimethyl ether reactor and recycled upstream of the natural gas reformer.

In such systems and methods, the amount of steam fed to the system may be controlled depending on the feed composition, particularly the amount of CO2 and hydrocarbons native to the feed to the natural gas reformer, to leverage the water-gas-shift reactions occurring in the dimethyl ether reactor to produce carbon dioxide in sufficient quantities to supplement the native CO2 content in the natural gas feed. In particular, steam may be added in sufficient quantities to achieve a Mm value of 1.4 to 1.8, or more preferably 1.5 to 1.65 wherein $Mm=(H2-CO2+H2O)/(CO+CO2-H2O)$ and H2 is moles of H2 fed to the dimethyl ether reactor, CO2 is moles of CO2 fed to the dimethyl ether reactor, CO is moles of CO fed to the dimethyl ether reactor and H2O is moles of H2O fed to the dimethyl ether reactor.

As used herein, "carbon efficiency" describes the material efficiency of the system in converting hydrocarbons to dimethyl ether, and as used herein, is calculated by dividing the number of carbon atoms present in the form of dimethyl ether as an effluent of the system or method by the total number of carbon atoms that are fed to the system, including carbons added for fuel to produce process heat streams, multiplied by 100%. It has been surprisingly discovered that in the integrated systems and methods of the present invention, carbon efficiency can be controlled by the amount of steam that is cofed to the dimethyl reactor with the syngas. In particular, carbon efficiency can be improved by providing sufficient steam to the dimethyl ether reactor such that carbon dioxide is produced in the dimethyl ether reactor in sufficient quantities to recycle back to the natural gas reformer (such as a reverse flow reactor) to produce a syngas comprising CO and H2 in a mole ratio of about 1:1, such as from about 0.8:1 or from about 1.1:1. Thus, it may be appreciated that the precise amount of CO2 required for recycle may depend on the amount of CO2 present in the natural gas feed to the natural gas reformer. Advantageously, substantially all of the CO2 needed for achieving the desired ratio of CO and H2 from the reverse flow reactor can be obtained from recycle without requiring an additional source of CO2, i.e., essentially no make-up CO2 is required. At least 90%, or at least 95%, or at least 99% of the CO2 fed to the reverse flow reactor may be supplied from the CO2 recycle loop obtained downstream of the dimethyl ether reactor. Systems and methods disclosed herein may achieve a carbon efficiency of at least 85% or at least 90%.

The term "thermal efficiency" as used herein describes how well the system makes use of the heating value of natural gas supplied to the process and is calculated as the Lower Heating Value of Product of the process divided by the Lower Heating Value of Natural Gas supplied to the process, including natural gas supplied as feed to the reformer and fuel used for process heat. The lower heating value (also known as net calorific value) of a fuel is defined as the amount of heat released by combusting a specified quantity (initially at 25° C.) and returning the temperature of the combustion products to 150° C., which assumes the latent heat of vaporization of water in the reaction products is not recovered. It has been found that the thermal efficiency of the integrated methods and systems disclosed herein can be superior to conventional systems because fuels such as H2 that are generated or not consumed in the process can be recycled to the reverse flow reactor, where the fuel may be used to regenerate the bed in the reverse flow reactor instead of requiring additional natural gas a regeneration or heating fuel. Advantageously, systems and methods disclosed herein can achieve thermal efficiency of at least 70% or more or at least 75% or more.

The dimethyl ether reactor may contain a catalyst system for converting syngas to dimethyl ether. The term "catalyst system" as used herein can refer to one or more catalysts suitable for producing the reaction products from the feeds described. In the context of a dimethyl ether reactor, the catalyst system may include a first catalyst for converting CO and H2 into methanol and a second catalyst for converting methanol to dimethyl ether. The first catalyst may be a M1/M2/Al catalyst, wherein M1 can be Cu, Ag, Au, Ru, Rh, Pd, Re, Os, Ir, Pt, and M2 can be Ti, V, Cr, Mn, Fe, Co, Ni, Zn, rare earth metals La series and Y series. M1 can be single metal, or the combinations of the M1 metal mixtures, M2 can be single metal, or the combinations of the M2 metal mixtures. The second catalyst may be an acid catalyst, such as a zeolite, ion exchanged zeolite e.g. SAPO, alumina, alumina silicates, titania, zirconia, and mixtures of the combinations of the acidic components, e.g., WO3/ZrO2, ZrO2/SiO2, resins, MOFS, ZIFs. The acidic property can be Lewis acidity, or Bronsted acidity, and the combination of the both Lewis acidity and Bronsted acidity. The metal components can be mixed with acidic components, or impregnated onto acidic supports, or extruded with acidic components. By employing the catalyst for conversion of syngas to methanol and the catalyst for the dehydration of methanol to dimethyl ether in the same reactor, the immediate in-situ dehydration of methanol can be achieved, improving the performance of the acid catalyst. The catalyst system may be a physical mixture of the catalysts.

Systems and methods disclosed herein may also have a low hydrocarbon selectivity and/or a low oxygenate selectivity. The term "hydrocarbon selectivity" as used herein refers to the amount of paraffinic hydrocarbon product, e.g., C2 or greater, that are present in the dimethyl ether reactor effluent after syngas is contacted with the catalyst system, expressed in mole %. The term "oxygenate selectivity" as used herein refers to the amount of oxygenates, e.g., carboxylic acids, esters, ketones that are present in the dimethyl ether reactor effluent after syngas is contacted with the catalyst system, expressed in mole %. Steam may be supplied in an amount sufficient to achieve a hydrocarbon selectivity of less than 3 mole % or less than 2 mole % with the catalyst system. The amount of steam supplied may also be sufficient to achieve an oxygenate selectivity of less than 0.005% or less than 0.001%.

Overview of System and Method for Producing Dimethyl Ether from Natural Gas

Figure 1:
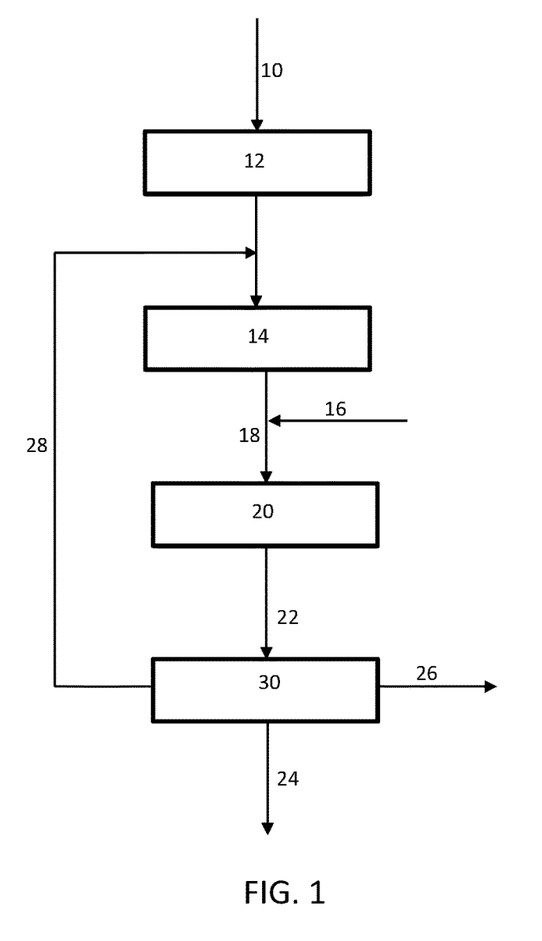
FIG. 1 is a flowchart, illustrating an integrated system and process for producing dimethyl ether from natural gas according to one or more embodiments of the present invention.

An exemplary method and system for the production of dimethyl ether from natural gas is illustrated in FIG. 1. Natural gas stream 10 is fed to a pretreater 12 to remove contaminants such as sulfur, chlorides and olefins. Pretreater 12 may be a single unit or, more likely, it is a series of units for removing the different types of contaminants found in the natural gas stream 12. For example, pretreater 12 may include a desulfurizing column for removing sulfur. Pretreater 12 can also include a guard bed to remove chlorides and/or a hydrotreater to covert olefins to paraffins.

The pretreated natural gas may then be fed to reformer 14, which may be a reverse flow reactor, to convert the natural gas to syngas 18. Recycled CO2 stream 28, which may also include recycled methane, can be fed with the treated natural gas to the reformer 14. It is noted that the pretreated natural gas stream may contain essentially zero CO2 (such as the gas in pipeline gas) or it may have a high CO2 content. Steam may also be added to the reformer 14 to promote the conversion of natural gas to syngas.

Steam 16 is co-fed to dimethyl ether reactor 20 with syngas 18 to produce product stream 22, which can include dimethyl ether, carbon dioxide, methane, hydrogen and other byproducts. The dimethyl ether reactor 20 may operate a temperature between about 200° C. and about 300° C. and a pressure between about 20 bar and about 40 bar.

The product stream 22 may be fed to one or more separators 30 to separate methane, carbon dioxide and other byproducts 26 from dimethyl ether 24. Methane and carbon dioxide may be recycled back to reformer 14 via recycle stream 28. The separation of the products may be accomplished using various separation processes including refrigeration, distillation/fractionation, high or low pressure flash separation, or membrane separation.

Direct Dimethyl Ether ("DME") Synthesis

Direct DME synthesis may be performed by converting syngas to methanol (Eq. 1) with the in-situ dehydration of methanol to DME (Eq. 3). Advantageously, both reactions can occur in the same reactor such that the methanol is nearly instantaneously dehydrated to DME as it is produced. In addition, a water gas shift reaction (Eq. 2) is typically present.

$$CO+2H_2 \leftrightarrow CH_3OH \ \Delta H_r=-90.84 \text{ kJ/mole} \quad \text{(Eq. 1)}$$

$$CO+H_2O \leftrightarrow CO_2+H_2 \ \Delta H_r=-41.27 \text{ kJ/mole} \quad \text{(Eq. 2)}$$

The equilibrium of the methanol reaction (Eq. 1) at high temperatures required to promote kinetics, is reactant favored and limits the overall syngas conversion in a traditional methanol process. However, the disclosed placement of the acid catalyst may enable the in-situ dehydration of methanol immediately after it is formed, maintaining the system sufficiently far from equilibrium limitations of Eq. 1 and may improve the per-pass conversion of syngas.

Various by-products can also be produced during the conversion of syngas to methanol (methane, water, carbon dioxide, formic acid) and the conversion of methanol to DME (acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of CO2 in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the catalyst stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3\text{—}O\text{—}CH_3+H_2O \ \Delta H_r=-21.26 \text{ kJ/mole} \quad \text{(Eq. 3)}$$

$$3CO+3H_2 \leftrightarrow CH_3\text{—}O\text{—}CH_3+CO_2 \ \Delta H_r=-246 \text{ kJ/mole} \quad \text{(Eq. 4)}$$

It has been found that carbon efficiency can be improved by controlling feed parameters, particularly the amount of water added to either the reforming reactor or the dimethyl ether reactor. Conventionally, syngas conversion process use factors like H2:CO ratio or M-value, (H2−CO2)/(CO+CO2), to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in amount to leverage the water-gas-shift reaction to co-produce CO2 (as needed to maximize carbon efficiency) in the dimethyl ether reactor. The amount of water added, is a function of the syngas composition (namely the amount of CO/CO2/H2/H2O present in the feed to the dimethyl ether reactor), which is a function of the steam reforming relative to the dry reforming carried out in the syngas reactor.

A preferred feed to the dimethyl ether reactor may be described with a modified M value, Mm:

$$\frac{H2 - CO2 + H2O}{CO + CO2 - H2O}$$

Figure 2:
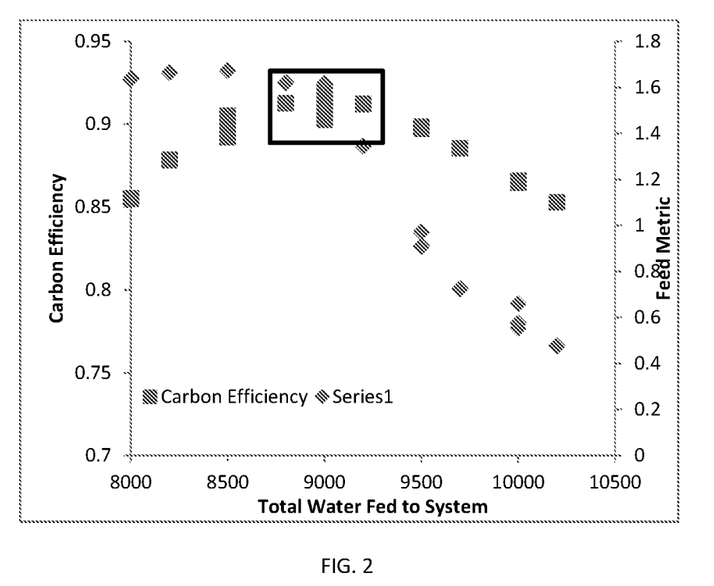
FIG. 2 is a graph, illustrating carbon efficiency as it correlates to a modified M value, $M_m$, for an integrated system for producing dimethyl ether from natural gas according to one or more embodiments of the present invention.
Figure 3:
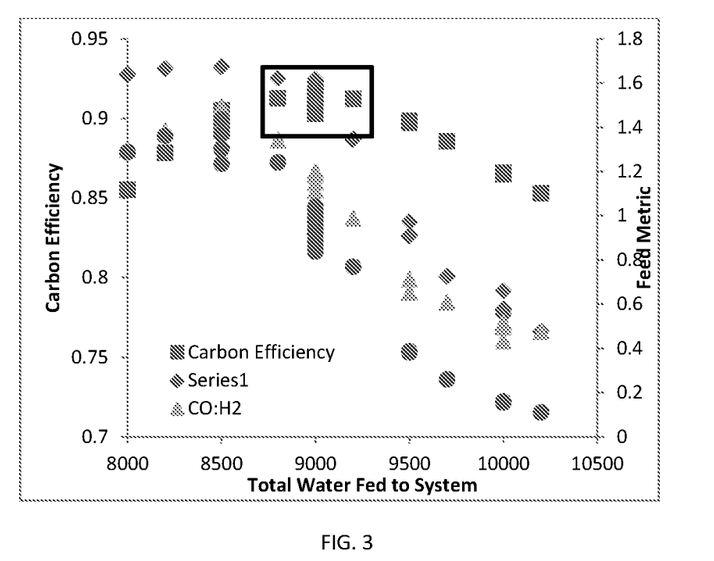
FIG. 3 is a graph, illustrating carbon efficiency as it correlates to other feed metrics for an integrated system for producing dimethyl ether from natural gas according to one or more embodiments of the present invention.

Water may be added to the process in total, either in the syngas reactor for steam reforming or in the DME reactor. Independent of how the water is split between the reactors this corresponds to a Modified M-value of about 1.6 (greater than 1.4, less than 1.8). This is illustrated in FIGS. 2 and 3.

Reforming Natural Gas to Syngas

Various reforming processes may be employed to produce syngas from such a natural gas feedstream, including partial oxidation, steam methane reforming, autothermal reforming, dry reforming or any combination thereof. Preferably, the natural gas stream is reformed using a reverse flow reactor.

Any natural gas feedstream can be reformed into syngas. As used herein, "natural gas" refers to a hydrocarbon feed that is predominantly C1 to C4 hydrocarbons, and it may be predominantly methane. The natural gas feedstream can also include carbon dioxide. For simplicity, examples used herein may make specific reference to methane; however, it should be understood that natural gas feed streams further comprising C2-C4 hydrocarbons may also be used. General equations for the dry reforming and steam reforming for such hydrocarbons are shown in Eq. 5 and Eq. 6, respectively.

$$C_nH_{2n+1}+CO_2 \to 2nCO+(n+1)H_2 \quad \text{(Eq. 5)}$$

$$C_nH_{2n+1}+H_2O \to nCO+(2n+1)H_2 \quad \text{(Eq. 6)}$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of CO2 and 2 moles of methane may produce 4 moles of CO and 4 mole of H2 as shown in Eq. 7.

$$2CO_2+2CH_4 \leftrightarrow 4CO+4H_2 \quad \text{(Eq. 7)}$$

If the products of Eq. 5 were then fed to the DME reactor with steam as a cofeed, the following products would be produced: 1 mole of DME, 2 moles of CO2 and 1 mole of H2 (Eqs. 4 and 2).

The reverse flow reactor for reforming the natural gas to syngas may operate at a temperature between 300° C. and 1400° C. and a pressure range between 1 bar and 100 bar.

Separation

The effluent from the dimethyl ether reactor may be separated into dimethyl ether and CO2, as well as any unreacted CH4, CO, H2 and other byproducts. Any one or combination of separation processes may be employed to perform such separations including, but not limited to, refrigeration, distillation/fractionation, flash separation and membrane separation. The CO2, CH4, and any unreacted intermediates may be recycled as described herein.

Recycle

Advantageously, recycle streams having desirable compositions can be obtained from separation processes downstream of the dimethyl ether reactor. These recycle streams can be used to improve the carbon efficiency of the integrated system and/or can provide other advantages.

In any embodiment, CO2 and CH4, and optionally CO, recovered downstream of dimethyl ether reactor may be recycled upstream of the syngas generation reactor. The CO2 may be provided in sufficient quantities such that when added to the CO2 native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the CO2 and CH4, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

Example One

Catalyst Preparation

Four different acid catalysts were prepared for evaluation—Catalysts A-D. Catalyst A was self-bound aluminum oxide catalyst that was calcined at 600° C. Catalyst B was a 65 wt % HZSM-5-5B and 35 wt % Al2O3 fixed bed catalyst. Catalyst C was 1.2 wt % Phosphorous on self-bound H-ZSM-5b phosphorous-stabilized catalyst. Catalyst D was MCM-49. Catalyst E is a catalyst suitable for converting syngas to methanol.

The catalysts were dried under pure N2 at 200° C. for 12 hours and then activated at 5 barg by introducing H2 into the N2 flow at different temperature steps.

Dry Feed Testing

Each acid catalyst A-D was loaded into the reactor with syngas to methanol catalyst (Catalyst E) at a 1:1 by weight loading ratio. For each catalyst configuration A/E-D/E, the reactor was run at 1000 LHSV at 250° C. with a feed having a composition of 10 vol % Ar, 2.7 vol % CH4, 8.4 vol % CO2, 39.35 vol % CO, and 39.35 vol % H2.

Wet Feed Testing

Each catalyst configuration A/E-D/E evaluated in the dry feed testing was also evaluated with a wet feed. For wet feed testing of each catalyst configuration A/E-D/E, the reactor was run at 1000 LHSV at 250° C. with a feed having a composition of 10 vol % Ar, 1.2 vol % CH4, 3.9 vol % CO2, 36.7 vol % CO, and 38 vol % H2 and 10.2 vol % H2O.

Product Analysis

Figure 4:
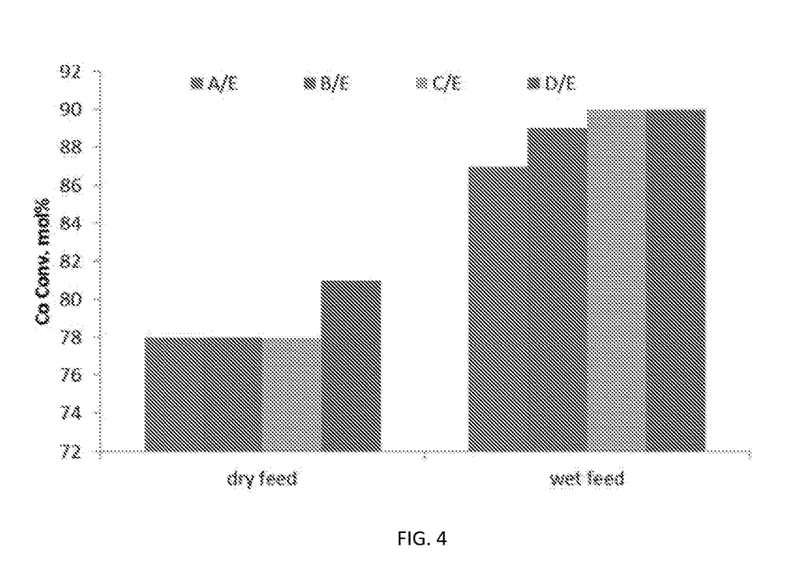
FIG. 4 is a graph, illustrating CO conversion for various catalyst configurations subjected to dry and wet feed testing.
Figure 5:
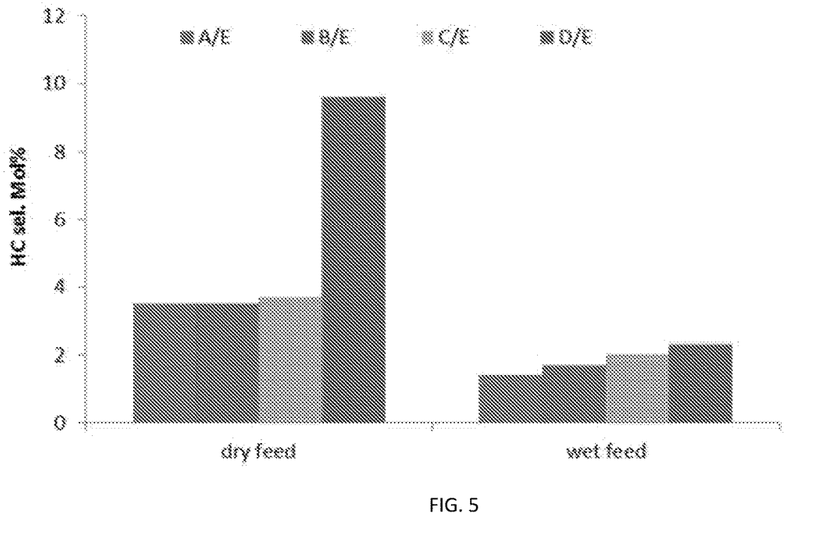
FIG. 5 is a graph, illustrating hydrocarbon selectivity for various catalyst configurations subjected to dry and wet feed testing.
Figure 6A:
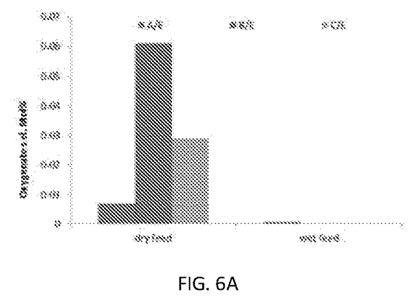
FIGS. 6A and 6B are graphs, illustrating oxygenate selectivity for various catalyst configurations subjected to dry and wet feed testing.
Figure 6B:
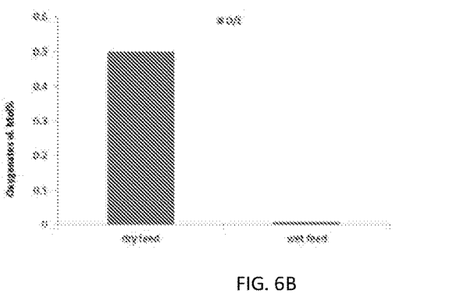

The product streams were analyzed by gas chromatography. FIG. 4 illustrates CO conversion, expressed in mole %, for each catalyst configuration in each of the dry feed testing and the wet feed testing. This illustrates that CO conversion is higher when steam is added to the process. FIG. 5 illustrates hydrocarbon selectivity, expressed in mole %, for each catalyst configuration in each of the dry feed testing and the wet feed testing. This illustrates that hydrocarbon selectivity is decreased by at least 50% when steam is co-fed to the process in comparison to a dry feed. FIG. 6 illustrates oxygenate selectivity, expressed in mole %, for each catalyst configuration in each of the dry feed testing and wet feed testing. This illustrates that oxygenate selectivity is dramatically decreased when steam is co-fed to the process.

Example Two

Each catalyst configuration A/E-D/E of Example One was tested at three different reactor temperatures (235° C., 250° C., and 275° C.) at 1000 LHSV with the dry and wet feeds of Example One.

Figure 7A:
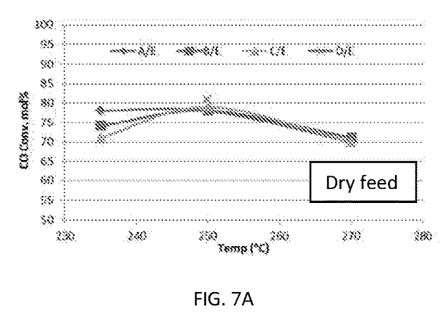
FIGS. 7A and 7B are graphs, illustrating the impact of temperature on CO conversion for various catalyst configurations subjected to dry and wet feed testing.
Figure 7B:
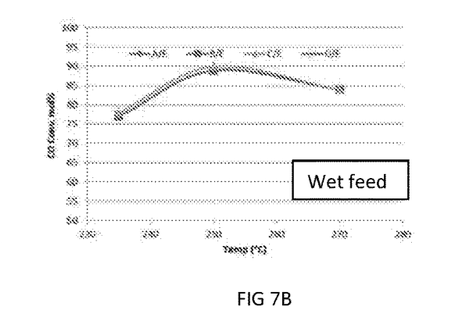
Figure 8A:
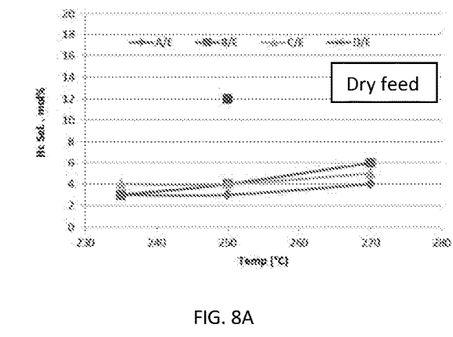
FIGS. 8A and 8B are graphs, illustrating the impact of temperature on hydrocarbon selectivity for various catalyst configurations subjected to dry and wet feed testing.
Figure 8B:
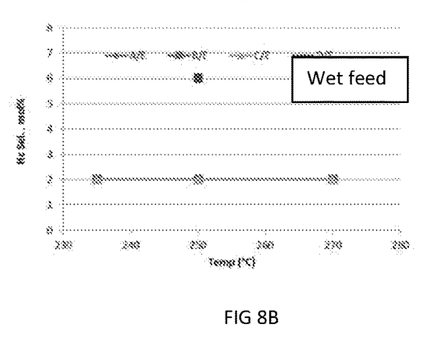
Figure 9A:
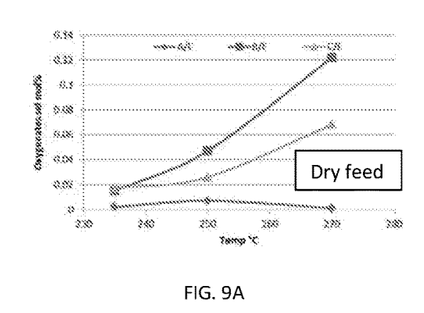
FIGS. 9A and 9B are graphs, illustrating the impact of temperature on oxygenate selectivity for various catalyst configurations subjected to dry and wet feed testing.
Figure 9B:
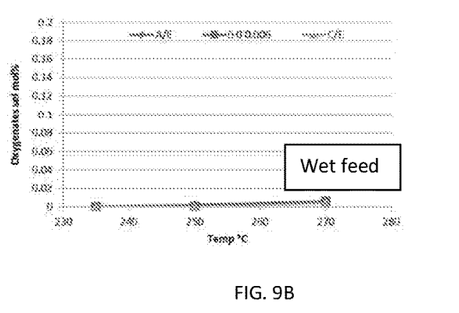

FIG. 7 illustrates the impact of temperature on CO conversion, expressed in mole %, for each catalyst configuration in each of the dry feed testing and the wet feed testing. This illustrates that co-feeding steam to the reactor improves the CO conversion for each of the three temperatures evaluated. FIG. 8 illustrates the impact of temperature on hydrocarbon selectivity, expressed in mole %, for each catalyst configuration in each of the dry feed testing and the wet feed testing. This illustrates that co-feeding steam to the reactor reduces the hydrocarbon selectivity for each of the three temperatures evaluated. FIG. 9 illustrates the impact of temperature on oxygenate selectivity, expressed in mole %, for each catalyst configuration in each of the dry feed testing and the wet feed testing. This illustrates that co-feeding steam to the reactor reduces the selectivity for the formation of oxygenates for each of the three temperatures evaluated.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

The invention claimed is:

1. An integrated method for the production of dimethyl ether comprising:
   reforming natural gas to syngas in a first reactor;
   contacting the syngas produced in the first reactor with a catalyst system in a second reactor to produce dimethyl ether and carbon dioxide; and
   supplying steam as a cofeed to at least one of the first reactor and the second reactor in an amount sufficient to achieve a $M_m$ value of 1.4 to 1.8 wherein $M_m=(H_2-CO_2+H_2O)/(CO+CO_2-H_2O)$ and $H_2$ is moles of $H_2$ fed to the second reactor, $CO_2$ is moles of $CO_2$ fed to the second reactor, CO is moles of CO fed to the second reactor and $H_2O$ is moles of $H_2O$ fed to the second reactor,
   wherein the first reactor is a reverse flow reactor.

2. The method of claim 1, further comprising recycling carbon dioxide produced in the second reactor to the first reactor.

3. The method of claim 1, wherein the method has a carbon efficiency is at least 85%.

4. The method of claim 3, wherein the method has a carbon efficiency is at least 90%.

5. The method of claim 1, wherein the steam is supplied in an amount sufficient to achieve a hydrocarbon selectivity of less than 3 mole % in the second reactor with the catalyst system.

6. The method of claim 1, wherein the hydrocarbon selectivity is less than 2 mole % with the catalyst system.

7. The method of claim 1, further comprising separating the carbon dioxide from dimethyl ether before recycling the carbon dioxide to the first reactor.

8. The method of claim 1, wherein the syngas is converted to methanol and the methanol is dehydrated to dimethyl ether in the second reactor.

9. The method of claim 1, wherein the steam is supplied in an amount sufficient to achieve a thermal efficiency of at least 70%.

10. The method of claim 1, wherein the steam is supplied in an amount sufficient to achieve a oxygenate selectivity of less than 0.005 mole %.

11. The method of claim 10, wherein the oxygenate selectivity of less than 0.001 mole %.

12. The method of claim 1, wherein the syngas comprises CO and $H_2$ in a CO:$H_2$ mole ratio from about 0.8:1 to about 1.1:1.

* * * * *